United States Patent

Caringi et al.

Patent Number: 5,262,511
Date of Patent: Nov. 16, 1993

[54] BRANCHED AROMATIC CARBONATE POLYMER

[75] Inventors: Joseph J. Caringi, Niskayuna, N.Y.; Luca P. Fontana, Evansville, Ind.; John R. Campbell, Clifton Park, N.Y.

[73] Assignee: General Electric Co., Pittsfield, Mass.

[21] Appl. No.: 845,092

[22] Filed: Mar. 3, 1992

[51] Int. Cl.$^5$ .................. C08G 63/00; C08G 63/02
[52] U.S. Cl. ...................... 528/176; 525/462; 528/183; 528/184; 528/188; 528/272
[58] Field of Search .............. 528/272, 176, 183, 184, 528/188; 525/462

[56] References Cited

U.S. PATENT DOCUMENTS

| | | | |
|---|---|---|---|
| 2,999,835 | 9/1961 | Goldberg | 524/267 |
| 3,028,365 | 4/1962 | Schnell et al. | 528/198 |
| 3,153,008 | 10/1964 | Fox | 526/71 |
| 3,169,121 | 2/1965 | Goldberg | 528/194 |
| 4,465,820 | 8/1984 | Miller | 528/194 |
| 4,737,573 | 4/1988 | Silva et al. | 528/371 |
| 4,743,676 | 5/1988 | Silva et al. | 528/371 |
| 4,983,706 | 1/1991 | Fontana et al. | 528/176 |
| 5,025,081 | 6/1991 | Fontana et al. | 528/176 |

Primary Examiner—John Kight, III
Assistant Examiner—T. Mosley

[57] ABSTRACT

A compound of the formula

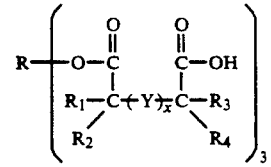

wherein

R is a hydrocarbon of three to about 50 carbon atoms and the residue of the reaction of triol R(OH)$_3$ with the anhydride of Formula II;

Y is CR$_5$R$_6$, O,S,NCH$_3$ wherein R$_5$ and R$_6$ are the same or different and are hydrogen, alkyl of one to three carbon atoms, inclusive, or phenyl;

x is O or 1;

R$_1$, R$_2$, R$_3$, and R$_4$ are the same or different and are selected from the group consisting of hydrogen, phenyl or aliphatic of one to about twenty carbon atoms, inclusive, and R$_2$ and R$_4$ joined together form a normal alkylene or alkenylene chain of two to about six carbon atoms, inclusive, unsubstituted or substituted with one to six alkyl groups having from one to about four carbon atoms, inclusive.

a process to make the compounds;

and branched aromatic carbonate polymers having incorporated therein in the branching component a compound of the above formula.

20 Claims, No Drawings

BRANCHED AROMATIC CARBONATE POLYMER

This invention relates to tricarboxylic compounds that have utility as branching agents for the manufacture of novel randomly branched aromatic carbonate polymers. These randomly branched aromatic carbonate polymers have excellent thermal resistance, stability, hydrolytic stability, high melt strength and enhanced light stability as compared to other branched polycarbonates. These desirable properties make the novel branched carbonate polymers particularly useful for the fabrication of blow molded articles although they may be employed for diverse molding applications such as profile extrusion.

BACKGROUND OF THE INVENTION

Polycarbonates are well known, commercially important materials which are produced in large quantities. Such polymers are typically prepared by reacting a carbonate precursor with a dihydric phenol to provide a linear polymer consisting of units of the dihydric phenol linked to one another through carbonate linkages. These polymers have outstanding mechanical, thermal, and optical properties such as high tensile strength, optical clarity (transparency), thermal and dimensional stability and impact strength.

These aromatic polycarbonates differ from most thermoplastic polymers in their melt rheology behavior. Most thermoplastic polymers exhibit non-Newtonian flow characteristics over essentially all melt processing conditions. Newtonian flow is defined as the type of flow occurring in a liquid system where the rate of shear is directly proportional to the shearing force. However, in contrast to most thermoplastic polymers, polycarbonates prepared from dihydric phenols exhibit Newtonian flow at normal processing temperatures and shear rates below 300 reciprocal seconds.

Two other characteristics of molten thermoplastic polymers are considered to be significant for molding operations: melt elasticity and melt strength. Melt elasticity is the recovery of the elastic energy stored within the melt from distortion or orientation of the molecules by shearing stresses. Melt strength may be simply described as the tenacity of a molten strand and indicates the ability of the melt to support a stress. Both of these characteristics are important in extrusion blow molding, particularly in fabrication by extrusion blow molding. Non-Newtonian flow characteristics tend to impart melt elasticity and melt strength to polymers thus allowing their use in blow molding fabrication. In the usual blow molding operation, a tube of a molten thermoplastic is extruded vertically downward into a mold, followed by the introduction of a gas, such as air, into the tube thus forcing the molten plastic to conform to the shape of the mold. The length of the tube and the quantity of material forming the tube are limiting factors in determining the size and wall thickness of the object that can be molded by this process. The fluidity of the melt obtained from bisphenol-A polycarbonate, or the lack of melt strength as well as the paucity of extrudate swelling, serve to limit blow molding applications to relatively small, thin walled parts. Temperatures must generally be carefully controlled to prevent the extruded tube from falling away before it attains the desired length and the mold is closed around it for blowing. Consequently, the Newtonian behavior of polycarbonate resin melts has severely restricted their use in the production of large hollow bodies by conventional extrusion blow molding operations as well as the production of various other shapes by profile extrusion methods.

Thermoplastic randomly branched polycarbonates exhibit unique properties of non-Newtonian flow, melt elasticity and melt strength which permit them to be used to obtain such articles as bottles which were not heretofore easily or readily produced with linear polycarbonates. The thermoplastic, randomly branched polycarbonates can be prepared by reacting the branching agent with a dihydric phenol and a carbonate precursor.

SUMMARY OF THE INVENTION

In accordance with the invention, there are multifunctional compounds useful as branching agents in preparation of aromatic carbonate polymers and of the structure

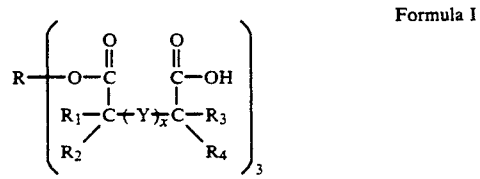

Formula I wherein
y is $CR_5R_6$, O,S,$NCH_3$; wherein $R_5$ and $R_6$ are the same or different and are hydrogen, alkyl of one to three carbon atoms, inclusive or phenyl;

x is O or 1;

R is a hydrocarbon of three up to about 50 carbon atoms, and is the residue of the reaction of triol R—(OH)$_3$ of Formula III;

$R_1$, $R_2$, $R_3$, and $R_4$ are the same or different and are hydrogen, phenyl or aliphatic of one to about twenty carbon atoms, inclusive or $R_2$ and $R_4$ joined together form a normal alkylene or alkenylene chain of two to about six carbon atoms, inclusive, unsubstituted or substituted with one to six alkyl groups having from one to about four carbon atoms, inclusive.

R is aliphatic, aromatic, or aliphatic aromatic or a substituted aliphatic, aromatic or aliphatic aromatic. R includes the acylic aliphatic moieties and the cycloaliphatic moieties. The acylic aliphatic moieties are preferably those containing from 3 to about 20 carbon atoms in either a straight chain or branched chain. They are preferably saturated. The cyclic aliphatic moieties are preferably those containing from 4 to about 8 ring carbon atoms. These cyclic aliphatic moieties may contain alkyl substituent groups on the ring carbon atoms, and the hydroxyl groups may be bonded to either the ring carbon atoms or to the alkyl substituent groups, or to both.

The aliphatic-aromatic hydrocarbon moieties represented by $R_4$ are those containing an aromatic portion which preferably contains from 6 to 24 ring carbon atoms, i.e., phenyl, naphthyl, and biphenyl, and an aliphatic portion bonded to the ring carbon atoms of the aromatic port&on with the hydroxyl groups being present on either or both the aliphatic or aromatic portion.

Aromatic includes any aromatic ring such as phenyl, napthyl, biphenyl and the like and is preferably four ring systems or less.

The substituted aliphatic, substituted aliphatic aromatic and substituted aromatic moieties represented by $R_4$ are those which contain substituent groups on the hydrocarbon moieties, preferably from 1 to about 4 substituent groups. The preferred substituent groups are the halogens, preferably chlorine and bromine, and nitro groups. When more than one substituent group is present they may be the same or different.

$R_1$, $R_2$, $R_3$ and $R_4$ are preferably hydrogen or alkyl or alkenyl of one to eight carbon atoms inclusive or when $R_2$ and $R_4$ are joined together form a normal, unsubstituted alkylene or alkenylene chain of two to s x carbon atoms, more preferably two to four carbon atoms. The more preferred upper limit of R, $R_1$, $R_2$, $R_3$ and $R_4$ is six carbon atoms, inclusive.

The most preferred group of compounds is where R is propyl, $R_1$ and $R_3$ are hydrogen and $R_2$ and $R_4$ are joined together in an alkylene chain of four carbon atoms or an alkenylene chain of four carbon atoms, particularly where the double bond is at the 4-5 carbon atom position.

The term aliphatic as used in this application means branched or normal alkyl, branched or normal alkenyl, cycloalky or cycloalkenyl. Of the unsaturated groups, monoalkenyl or monocycloalkenyl is preferred. Cycloalkyl or cycloalkenyl should have a minimum of four carbon atoms in the ring.

The most preferred branching agent is where R is propyl, $R_1$, and $R_3$ are hydrogen and $R_2$ and $R_4$ are joined together in a straight alkenylene chain of four carbon atoms wherein the double bond is at the 4-5 carbon position. The Chemical Abstract Index name would be 4-Cyclohexene-1,2-dicarboxylic acid, 2-[[[(6-carboxy-3-cyclohexen-1-yl)carbonyl]oxy]methyl]-2-ethyl-1,3-propanediyl ester.

A further aspect of the invention is the preparation of the above triacids of Formula I by the reaction of an aliphatic triol

 Formula II wherein R is defined as above with the proviso that only one hydroxyl can be on any single carbon atom with an acid anhydride of the formula

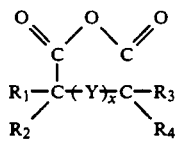 Formula III wherein y, x, $R_1$, $R_2$, $R_3$ and $R_4$ are defined as above.

A still further aspect of the invention is a thermoplastic randomly branched aromatic carbonate polymer having incorporated therein a branching component in an amount sufficient to produce a thermoplastic randomly branched aromatic carbonate polymer which is substantially free of crosslinking said branching agent comprising one or more compounds of Formula I above.

DETAILED DESCRIPTION OF THE INVENTION

The aliphatic tricarboxylic acids useful in the invention are those of Formula I above.

The method of preparing the tricarboxylic acids of the invention is very simple and effective - the reaction of the trialcohol of Formula II with the anhydride of Formula III. The reaction may be carried out in the presence of a solvent or neat. If a solvent is employed suitable solvents include methylene chloride, preferably with a catalyst, toluene, chlorobenzene and xylene. It is preferred to carry out the reaction in a neat melt manner at an elevated temperature which melts both reactants. Generally, a high degree of completion of the reaction is observed, sometimes upwards of 99.5% or higher. Temperatures of from about 105° to 125° C. can be generally employed. Although not necessary, a catalyst can be employed in the reaction. Catalytic quantities of an acid such as sulfuric, paratolunesulfonic acid and methanesulfonic acid or a salt such as sodium or potassium acetate are effective. It is readily apparent because of the stereochemistry possible through the number of chiral centers present as asymmetric carbon atoms or potential epimers that a multiplicity of specific stereoisomers such as diastereomers can be formed. Any of these stereoisomers or all may be present as a mixture or a diastereomer can prevail. The Formula I is intended to cover all stereoisomeric forms possible. The aliphatic triacids may be prepared in isolated form for use as branching agents for polycarbonates or if desired, mixtures of these branching agents may be employed alone or with other branching agents.

Examples of the triols include and are not limited to $\alpha',\alpha',\alpha'$-(tris(4-hydroxyphenyl)-1,3,5-triisopropylbenzene, 1,3,5-tris(4-hydroxyphenyl)-benzene, 1,1,1-tris(4-hydroxyphenyl)-ethane, tris(4-hydroxyphenyl) phenylmethane, 1,1,1-trimethylol ethane, 1,1,1-trimethylol propane 1,1,1-trimethylol butane, 1,2,3-trimethylol propane, 1-[$\alpha$-methyl-$\alpha$-(4'-hydroxyphenyl) ethyl]-4-[$\alpha'$,-$\alpha'$,-bis(4''-hydroxyphenyl)ethyl]benzene, glycerol, 1,2,3 butanetriol, 1,1,2 trimethylol ethane, and 1,3,5 tri hydroxy benzene.

The triacids of the instant invention may be used to make novel branched aromatic carbonate polymer having an IV of about 0.3 to 1.0 dl/g as measured in methylene chloride at 25° C. These branched carbonate polymers are substantially free of crosslinking.

In the preparation of the novel thermoplastic randomly branched polycarbonates of this invention, the amount of the branching compound which is reacted with a dihydric phenol and a carbonate precursor is critical to the extent that the amount employed must be sufficient to produce a true thermoplastic randomly branched aromatic carbonate polymer which is substantially free of crosslinking. If an amount of branching compound employed is less than 0.01 mole percent, based upon the moles of the dihydric phenol employed, the resulting polymer will not exhibit the degree of non-Newtonian melt characteristics desired for blow molding and/or melt extrusion purposes. Preferably, it is desirable to employ 0.01 to about 3.0 and more particularly, 0.01-1.0 mole percent of the branching compound, based upon the total moles of dihydric phenol.

The dihydric phenols that can be employed in the practice of this invention include bis(4-hydroxyphenyl) methane, 1,1-bis(4-hydroxyphenyl)ethane, 2,2-bis(4-hydroxyphenyl)propane, also called bisphenol-A or BPA, 2,2-bis(4-hydroxy-3-methylphenyl)propane, 3,3-bis(4-hydroxyphenyl)pentane, 2,2-bis(4-hydroxy-3-chlorophenyl)propane, 2.2-bis(4-hydroxy-3,5-dibromophenyl)propane, 1,1-bis(4-hydroxyphenyl)cyclohexane, p,p'-dihydroxydiphenyl, 3,3'-dichloro-4,4'-dihydroxydiphenyl, bis(4-hydroxyphenyl)ether, bis(4-hydroxyphenyl) sulfone, bis(3,5-dimethyl-4-hydroxyphenyl)- sulfone, resorcinol, hydroquinone; 1,4-hydroxy-2,5-dichlorobenzene, 1,4-dihydroxy-3-methylbenzene, bis(4-hydroxyphenyl)sulfoxide, bis(4-hydroxyphenyl)-sulfide, bis(3,5-dimethyl-4-hydroxyphenyl)sulfoxide, and the like. A variety of additional dihydric phenols can also be employed such as are disclosed in U.S. Pat. Nos. 2,999,835; 3,028,365 and 3,153,008. A specific diphenol is derived from reacting hydrogenated isophorone with phenol, thereby making trimethylcyclohexyl bisphenol (bisphenol TMC). It is, of course, possible to employ two or more different dihydric phenols or a copolymer of a dihydric phenol with glycol or with hydroxy or acid terminated polyester, or with one or more dibasic acids in the event a polycarbonate copolymer or copolyestercarbonate rather than a homopolymer is desired for use in the preparation of the branched polymers of this invention. The preferred dihydric phenol is bisphenol-A.

Further with respect to copolyestercarbonates, the copolyestercarbonates disclosed in Goldberg U.S. Pat. No. 3,169,121, Miller U.S. Pat. No. 4,465,820 and the Fontana et. al, U.S. Pat. Nos. 4,983.706 and 5,025,081, all incorporated by reference into this patent application can all be branched in accordance with this invention. The dicarboxylic acids which bring about the ester group in the copolyestercarbonate when reacted with a dihydric phenol and a carbonate precursor are aromatic dicarboxylic acids or aliphatic dicarboxylic acids. Examples of the aromatic acids include the phthalic acids such as o-phthalic, isophthalic acid and terephthalic acid. Naphthyl diacids can also be employed. Generally the iso and/or terephthalic acids are preferred. When utilizing a solvent system for example in the interfacial process, the diacids are preferably in their acid halide forms because of solubility issues. Examples of the aliphatic diacids include those normal or branched alpha omega acids having from about six to eighteen carbon atoms, inclusive, see Fontana. Useful examples of such acids include adipic, azelaic, suberic, sebacic, dodecanedioic and the like. Such acids can be incorporated into the copolyestercarbonate through reaction in their metal salt form.

The carbonate precursor employed can be either a carbonyl halide, a haloformate or a diaryl carbonate. Thus the carbonyl halides can be carbonyl chloride, carbonyl bromide, and mixtures thereof. The haloformates suitable for use include mono- or bishaloformates of dihydric phenols (bischloroformates of hydroquinone, monochloroformate of bisphenol-A, etc.) or bishaloformates of glycols (bishaloformates of ethylene glycol, neopentyl glycol, polyethylene glycol, etc.). When using bishaloformates, equimolar amounts of free dihydric phenols can be used to effect polymerization. When polymerizing monohaloformates of diphenols no free diphenol is required. Other bishaloformate methods such as disclosed in Silva et. al, U.S. Pat. Nos. 4,737,573 and 4,743,676 are also applicable to preparing compositions of this invention. While other carbonate precursors will occur to those skilled in the art, carbonyl chloride, also known as phosgene is preferred.

The polymerization of dihydric phenols to high molecular weight polycarbonates may be carried out by any conventional method known in the art. For example, phosgene can be introduced into a solution of the diphenol in organic bases, such as pyridine, triethylamine, dimethylaniline or into solutions of the diphenol in suitable organic solvents, such as benzene, toluene, chlorobenzene, methylene chloride, carbon tetrachloride and the like, with the addition of acid binding agents.

In the most widely practiced polymerization process phosgene is introduced into an aqueous solution of the alkali metal salt of the diphenol in the presence of methylene chloride and a phase-transfer catalyst as well as a molecular weight regulator, usually a monofunctional phenol. The branching compounds of this invention can be formulated directly into the reaction mixture to be polymerized to branched polycarbonates. They can be added directly with other dihydric phenols or later. Because of their appropriate solubilities, the branching agents can be added as the carboxylic acids per se. However they can also be added as the alkali or alkaline earth metal salts, for example sodium, potassium, calcium and the like or as the amine salts. Examples of amines which can be utilized include the trialkylamines such as triethylamine, triproplyamine, amidines, quanidine, pyridine, 2-ethylpyridine and the like. An advantage of using the amine salt, particularly triethylamine salt of the branching agent is that the polymerization reaction can be carried out in the same reactor as the preparation of the branching compound. The amine, particularly triethylamine, not only is the salt of the branching component but also functions as the catalyst for the polymerization. No additional catalyst need be employed.

The reaction between the halogen containing carbonate precursor and the dihydric phenol and the branching agent when carried out by the interfacial method in accordance with this invention is conducted in the presence of an inert organic solvent which is essentially immiscible with water and does not deleteriously affect the formed polymer. Examples of suitable organic solvents ae methylene chloride, ethylene dichloride and chlorobenzene.

The alkali metal hydroxide which can be employed in the polymerization process can be any of the alkali metal hydroxides selected from the groups consisting of the alkali group and the alkaline earth groups. Specifically, these include potassium hydroxide, sodium hydroxide, lithium hydroxide, calcium hydroxide, magnesium hydroxide and the like.

The interfacial, or phase transfer catalysts, which can be employed in the polymerization process can be any of the suitable catalysts that aid the polymerization of dihydric phenols with phosgene. Suitable catalysts include tertiary amines such as triethylamine, tripropylamine, N,N-dimethylaniline and the like; quarternary ammonium compounds such as tetraethylammonium chloride, cetyl triethyl ammonium bromide, tetra-n-neptylammonium iodide, tetra-n-propyl ammonium chloride tetramethylammonium chloride, tetramethylammonium hydroxide, tetra-n-butylammonium iodide, benzyltrimethylammonium chloride and the like; and quarternary phosphonium compounds such as n-butyl triphenyl phosphonium bromide and tetrabutyl phosphonium chloride and the like.

The molecular weight regulators which can be employed in the interfacial process include monohydric phenols such as phenol, chroman-I [4-(2,4,4-trimethylchromanyl)phenol], p-t-butyl phenol, p-cumyl phenol, an the like. Preferably, phenol or p-cumyl phenol are employed as the molecular weight regulator. An effective amount of a molecular weight regulator that will give an I.V. of about 0.3 to 1.0 dl/g in methylene chloride at 25° C. can be used. Generally, it is preferred to use from 2-5 mol %, and more preferably from 2.4-4.5 d mol % of phenol as the molecular weight regulator.

It is sometimes desirable to introduce reducing agents, such as sodium dithionite into the aqueous system in order to supress the formation of colored contaminants.

The aqueous interfacial polymerization method may be carried out at temperatures from ambient to about 50° C. However, higher temperatures are within the scope of this invention since the instant method is not temperature dependent.

The mixture can be converted into branched polycarbonates also by esterification with dialkyl, alkylaryl or diaryl carbonates and tri esters of the aliphatic tricarboxylic acids of the branching components. Although alkylesters having one to six carbon atoms, inclusive can be used, aromatic esters such as the triphenylester are preferred. The reaction can be carried out at elevated temperatures from about 50° C. to about 325° C, at atmospheric or at reduced pressure, in neat form, or in the presence of neutral diluents or in the presence of transesterification catalysts, such as metal oxides, hydroxides, carbonates and the like, as known in the art. When using aryl carbonates, phenols are generated in the transesterification process, so that no molecular weight regulators need be added to the reaction mixture. In fact the degree of polymerization is controlled by the extent of removal of the monohydroxylic coproducts, such as alcohols or phenols.

The branched aromatic carbonate polymers, when produced according to the instant invention by the interfacial polymerization technique, were recovered from the washed, neutral methylene chloride phase by steam precipitation and drying and were fed into an extruder operating at 265° C. and the extrudates were comminuted into pellets. When prepared by the transesterification method, the polymer melt was directly converted into extrudate and pellets.

The branched carbonate polymers produced according to the instant invention are soluble in selected organic solvents and can be worked into shaped articles from solutions, such as into films. Being thermoplastic, these branched carbonate polymers, can be easily fabricated by conventional shaping methods from melt, such as by extrusion, molding, blow-molding, lamination and the like.

The branched carbonate polymers of the invention may be combined with other polycarbonates or with thermoplastic polyesters such as polyethylene terephthalate or poly (1,4-butylene terephthalate). In addition, these branched carbonate polymers may be combined with reinforcing fillers such as filamentous glass or with non-reinforcing fillers, mold release agents, flame retardants, impact modifiers, extrusion aids, light stabilizers, flame retardants, foaming agents, such as those disclosed in U.S. Pat. No. 4,263,409 and Ger. Offen. 2,400,086 which are incorporated by reference and the like if desired.

The following examples are set forth to illustrate the invention and are not to be construed to limit the scope of the invention.

EXAMPLE 1

Melt synthesis of 4-Cyclohexene-1,2-dicarboxylic acid, 2-[[[(6-carboxy-3-cyclohexen-1-yl)carbonyl]oxy]-methyl]-2-ethyl-1,3-propanediyl ester (hereafter known as THMP/THPA). To a 3 liter resin kettle equipped with a mechanical stirrer and nitrogen inlet was added 149.4 g (1.113 mole) 2-ethyl-2-(hydroxy- methyl)-1,3-propanediol and 510.3 g (3.354 mole) cis-1,2,3,6-tetrahydrophthalic anhydride. The kettle was heated in a 120° C. oil bath to make a melt. Heating was continued with stirring for 18 hr. A sample was removed for nmr analysis and the reaction was found to be complete. After cooling to room temperature, the product was removed from the reactor.

EXAMPLE 2

Solution synthesis of tris (hydroxymethyl)ethane/-succinic anhydride (hereafter known as THME/SA). To a 500 ml resin kettle equipped with a mechanical stirrer, nitrogen inlet and condensor was added 14.334 g (0.119 mole) tris(hydroxymethyl) ethane, 36.30 g (0.363 mole) succinic anhydride, and 250 ml toluene. The mixture was heated at reflux for 18 hr. Upon cooling to room temperature, a sample of the oil layer was removed for nmr, which indicated that the reaction was complete. The toluene was decanted away and the oil was washed once with pentane. The remaining solvent was removed by evacuation of the resin kettle (−1 mm) while heating in a 125° C. oil bath for 1 hr. After cooling to room temperature, the viscous oil was removed.

EXAMPLE 3

Tris triethylammonium salt of THMP/THPA. To a 250 ml round-bottomed flask equipped with a magnetic stir bar, nitrogen inlet and condensor was added 4.998 g (0.03725 mole)2-ethyl-2-(hydroxymethyl)-1,3-propanediol, 17.002 g (0.11175 mole) tetrahydrophthalic anhydride, 60 ml methylene chloride, and 28.5 ml (20.69 g, 0.20448 mole) triethylamine. The mixture was heated in a 60° C. oil bath and quickly made a solution. Progress of the reaction was monitored by periodically removing an aliquot, quenching in dilute HCl, drying the organic layer, evaporation of solvent and recording the mnr spectrum to observe conversion of the anhydride. The reaction was complete after 3 hr.

EXAMPLE 4

THMP/THPA from a solution of its tris triethylammonium salt. A methylene chloride solution of the tris triethylammonium salt of THMP/THPA was added to a separatory funnel containing methylene chloride and dilute HCl. The organic layer was washed three additional times with dilute HCl, three times with water, dried over sodium sulfate, filtered and evaporated to give the solid free acid.

EXAMPLE 5

Branched polycarbonate from THMP/THPA. To a 500 ml 5-necked Morton flask equipped with a phosgene inlet, reflux condensor, nitrogen inlet, pH probe connected to a caustic addition controller, caustic inlet and mechanical stirrer was added 14.999 g (0.0657 mole) bisphenol A, 0.145 g (0.000246 mole, 0.37 mole % PBA) THMP/THPA, 120 ml methylene chloride, 100 ml deionized water, 2 ml of a solution of 1.664 g triethylamine in 25 ml methylene chloride (0.133 g, 0.00132 mole, 2.0 mole % BPA) and 2 ml of a solution of 2.319 g phenol in 25 ml methylene chloride (0.186 g, 0.00197 mole, 3.0 mole % BPA). Phosgene was passed through the mixture at a rate of 0.4 g/min, while maintaining a pH between 8 and 8.5. After 15 min, the pH was maintained between 10 and 10.5 for an additional 4.5 min, at which time the flow of phosgene was stopped. Excess phosgene was purged with a stream of nitrogen. The mixture was poured into a separatory funnel containing 1N HCl, and the layers were separated. The organic layer was washed twice with 1N HCl and ten times with water, precipitated in methanol, reslurried three times in methanol, and dried in a 105° C. vacuum oven for 18 hr.

EXAMPLE 6

Tris acid chloride of THME/SA. To a 100 ml round-bottomed flask equipped with a condensor and nitrogen inlet was added 4.88 g (0.0116 mole) THME/SA and 5.2 ml (8.48 g, 0.0712 mole) thionyl chloride. The mixture was heated in an oil bath maintained between 30°–40° C. until gas evolution was complete (−3 hr). The solution was cooled to room temperature, and excess thionyl chloride was removed under vacuum. The crude tris acid chloride was used without further purification.

EXAMPLE 7

Tris phenyl ester of THME/SA. A 0.0059 mole sample of the tris acid chloride was prepared as described above, cooled to room temperature, and diluted with 10 ml ether. To this solution was added 1.695 g (0.018 mole) phenol in 30 ml ether. An addition funnel was fitted above the condensor, and a solution of 2.3 ml (1.67 g, 0.0165 mole) triethylamine in 20 ml ether was added rapidly. The mixture was stirred at room temperature for 1 hr and poured into a separatory funnel containing dilute sodium bicarbonate. The organic layer was washed four times with water, dried over magnesium sulfate, filtered and evaporated. Product was obtained by chromatography of the residue on silica gel with 30% EtOAc/hexane.

EXAMPLE 8

Branched polycarbonate from THME/SA (pyridine solution). To a 500 ml 5-necked Morton flask equipped with a mechanical stirrer, phosgene inlet, reflux condenser, nitrogen inlet and two stoppers was added 25.000 g (0.1095 mole) bisphenol A, 0.309 g (0.00329 mole) phenol and 120 ml methylene chloride. A solution of 0.171 g (0.000407 mole) THME/SA in—10 ml pyridine was prepared and was washed into the flask so that a total of 27.5 ml (26.9 g, 0.34 mole) pyridine was used. Phosgene was passed through the solution at a rate of 0.6 g/min for 21 min 40 sec (13.0 g, 0.1313 mole). The reaction was purged of excess phosgene with a stream of nitrogen and diluted with an equal volume of methylene chloride. The solution was was washed six times with 1N HCl and four times with deionized water, precipitated into methanol, reslurried in water, rinsed once with water and dried in a 105° C. vacuum oven for 18 hr.

EXAMPLE 9

Branched polycarbonate from THME/SA (BCF process). To a 500 ml 5-necked Morton flask equipped with a phosgene inlet, reflux condenser, nitrogen inlet, pH probe connected to a caustic addition controller, caustic inlet and mechanical stirrer was added 25.002 g (0.1095 mole) bisphenol A, 100 ml methylene chloride, and 100 ml deionized water. Phosgene was passed through the mixture at a rate of 0.6 g/min for 21 min 40 sec, while maintaining a pH between 8 and 8.5. The reaction mixture became very thick, and the pH dropped to 4–5. Caustic was added to adjust the pH to 7. Excess phosgene was purged with a stream of nitrogen. Phenol (2 ml of a solution of 3.859 g in 25 ml methylene chloride, 0.309 g, 0.00328 mole, 3.0 mole % BPA) was added, along with 0.169 g (0.000402 mole, 0.37 mole % BPA) THME/SA and 2 ml of a solution of 2.770 g triethylamine in 25 ml methylene chloride (0.222 g, 0.00219 mole, 2.0 mole % BPA), both together in 10 ml methylene chloride. The pH was raised slowly to 10.5 by the addition of 50% NaOH. It continued to rise to 11.8 and was adjusted to 10.5 again by the addition of phosgene and caustic. The mixture was poured into a separatory funnel containing 1N HCl, and the layers were separated. The organic layer was washed twice with 1N HCl and three times with water, precipitated in methanol, reslurried in water, washed with water, and dried in a 105° C. vacuum oven for 18 hr.

EXAMPLE 10

Branched BPA polycarbonate using THMP/THPA branching component. To the 30-liter, glass vessel equipped with mechanical stirrer, gas inlet tube, pH electrode in recirculation sample loop, chilled reflux condenser, NaOH scrubber, solution reservoir and metering pump was added deionized water (8.0 L), methylene chloride (11.0 L), BPA (3196 g, 14.00 mol), tricarboxyclic acid branching agent THMP/THPA (0.0518 mol), p-cumylphenol (89.16 g, 0.42 mol), triethylamine (40 ml, 0.29 mol), and sodium gluconate (5 g). Phosgene was introduced to the vigorously agitated reaction mixture at a rate of 48 g/min for 18 minutes while a pH range of 8.0–9.0 was maintained by the addition of 50% NaOH. The pH was then increased and maintained in the range of 10.0–11.0 for additional 18 min (total phosgene 1728 g, 17.45 mole). The phosgene depleted solution was diluted to 10% solids with the addition of methylene chloride (ca. 14 L), and the aqueous brine and polymer solution were separated using a Westfalia liquid-liquid centrifuge. The organic phase was extracted twice with a continuous feed of 0.2N aqueous HCl followed by five deionized water washes or until solution ionic chloride levels were non-detectable and triethylamine content was less than 1 ppm. The extracted polymer solution was isolated by steam precipitation at a 1 L/min feed rate and 50 psig steam feed pressure. The water wet, coarse powder was chopped in a Fitzmill to achieve a more uniform particle size and dried in a hot nitrogen fed, fluid bed dryer (final powder temperature =250° F.).

EXAMPLE 11

Branched polycarbonate using TEA salt of THMP/THPA. To the 30-liter, glass vessel equipped with mechanical stirrer, gas inlet tube, pH electrode in recirculation sample loop, chilled reflux condenser, NaOH scrubber, solution reservoir and metering pump was added deionized water (8.0 L), methylene chloride (11.0L), BPA (3196 g, 14.00 mol), TEA salt solution (0.0518 mole branching agent, THMP/THPA, p-cumylphenol (89.16 g, 0.42 mol), and sodium gluconate (5 g). Phosgene was introduced to the vigorously agitated reaction mixture at a rate of 48 g/min for 18 minutes while a pH range of 8.0–9.0 was maintained by the addition of 50% NaOH. The pH was then increased and maintained in the range of 10.0–11.0 for additional 18 min (total phosgene 1728 g, 17.45 mole). The phosgene depleted solution was diluted to 10% solids with the addition of methylene chloride (ca. 14 L), and the aqueous brine and polymer solution were separated using a Westfalia liquid-liquid centrifuge. The organic phase was extracted twice with a continuous feed of 0.2 N aqueous HCl followed by five deionized water washes or until solution ionic chloride levels were non-detectable and triethylamine content was less than 1 ppm. The extracted polymer solution was isolated by steam precipitation at a 1 L/min feed rate and 50 psig steam feed pressure. The water wet, coarse powder was chopped in a Fitzmill to achieve a more uniform particle size and dried in a hot nitrogen fed, fluid bed dryer (final powder temperature =250° F.).

EXAMPLE 12

Branched polycarbonate using THMP/THPA BCF conditions. To the 30-liter, glass vessel equipped with mechanical stirrer, gas inlet tube, pH electrode in recirculation sample loop, chilled reflux condenser, NaOH scrubber, solution reservoir and metering pump was added deionized water (5.OL), methylene chloride (11.OL), BPA (3196 g, 14.00 mol), and sodium gluconate (5 g). Phosgene was introduced to the vigorously agitated reaction mixture at a rate of 50 g/min for 27 min (1350 g, 13.64 mole) while a pH range of 8.0–9.0 was maintained by the addition of 50% NaOH. Excess phosgene was removed by a nitrogen sparge (5 min), and p-cumylphenol (89.16 g, 0.42 mol) was added. The solution was stirred for 2 min and the pH ramped to a range of 9.5–10.5, at which time the triethylamine salt solution (0.0518 mole branching agent, THMP/THPA) was added over a 3–5 min period. A viscous white emulsion formed, which broke after 15 min of polymerization. Phosgene (2.00 mole) was added to complete the polymerization. The phosgene depleted solution was diluted to 10% solids with the addition of methylene chloride (ca. 14L), and the aqueous brine and polymer solution were separated using a Westfalia liquid-liquid centrifuge. The organic phase was extracted twice with a continuous feed of 0.2 N aqueous HCl followed by 13 deionized water washes, at which point it st.11 had a chloride level of 1 ppm by titration. No further isolation of the polymer from the bulk solution was attempted.

What is claimed is:

1. A compound of the formula

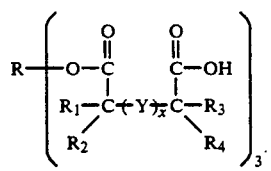

wherein

R is a hydrocarbon of from three to about 50 carbon atoms which compound is the product of the reaction of a triol of the formula $R(OH)_3$ with an anhydride of the formula:

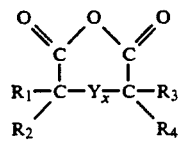

Y is $CR_5R_6$, O, S or $NCH_3$, wherein $R_5$ and $R_6$ are the same or different and are selected from the group consisting of hydrogen, alkyl of one to three carbon atoms, inclusive, and phenyl;

X is zero or 1;

$R_1$ and $R_3$ are the same or different and are selected from the group consisting of hydrogen, phenyl and aliphatic of one to about twenty carbon atoms, inclusive, and $R_2$ and $R_4$ are joined together to form an alkylene or alkenylene chain of two to about six carbon atoms, inclusive, unsubstituted or substituted with one to six alkyl groups each of said groups having from one to about four carbon atoms, inclusive.

2. The compound of claim 1 wherein R is aliphatic, aromatic, aliphatic aromatic or substituted aliphatic, substituted aromatic or substituted aliphatic aromatic of three to about twenty carbon atoms, inclusive; y is $CR_5R_6$.

3. The compound of claim 2 wherein R is aliphatic, the acyclic aliphatic is saturated, the cyclic aliphatic ring has four to about eight carbon atoms, inclusive, when R is aromatic there is a maximum of two aromatic rings; x is zero.

4. The compound of claim 3 wherein R is alkyl of three to about eight carbon atoms, inclusive; $R_1$, $R_2$, $R_3$ and $R_4$ are alkyl of one to eight carbon atoms, inclusive, alkenyl of two to eight carbon atoms, inclusive and when $R_2$ and $R_4$ are joined together form a normal, unsubstituted alkylene or alkenylene chain of two to six carbon atoms, inclusive.

5. The compound of claim 4 wherein the upper limit of carbon atoms in R, $R_1$, $R_2$, $R_3$ and $R_4$ is six carbon atoms, inclusive and when $R_2$ and $R_4$ are joined together the upper range is four carbon atoms, inclusive.

6. The compound of claim 5 wherein R is 1,1,1, trimethylene propyl, $R_1$ and $R_3$ are hydrogen, $R_2$ and $R_4$ are joined together in an alkylene chain or alkenylene chain of 4 carbon atoms, inclusive.

7. The compound of claim 6 wherein $R_2$ and $R_4$ are joined together in an alkylene chain of four carbon atoms with the double bond at carbon 4–5 position, the compound named 4-Cyclohexene-1,2-dicarboxylic acid, 2-[[[(6-carboxy-3-cyclohexen-1-yl)carbonyl]oxy]-methyl]-2-ethyl-1,3-propanediyl ester.

8. A method for preparing the compound of claim 1 wherein $R(OH)_3$ R is defined in claim 1 and having no one carbon atom of R bearing more than one hydroxyl is reacted with

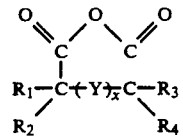

wherein y, x, R, $R_1$, $R_2$, $R_3$ and $R_4$ are defined as in claim 1.

9. The method of claim 8 wherein a solvent is present.

10. The method of claim 8 wherein no solvent is present.

11. The method of claim 8 wherein a catalyst is present.

12. A thermoplastic randomly branched aromatic carbonate polymer having incorporated therein a branching component in an amount sufficient to produce a thermoplastic randomly branched polycarbonate which is substantially free of crosslinking wherein the branching component comprises a compound of the formula

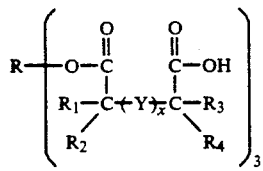

wherein

R is a hydrocarbon of from three to about 50 carbon atoms which component is the product of the reaction of a triol of the formula $R(OH)_3$ with an anhydride of the formula:

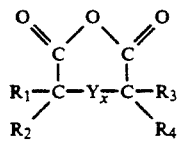

Y is $CR_5R_6$, O, S or $NCH_3$ wherein $R_5$ and $R_6$ are the same or different and are selected from the group consisting of hydrogen alkyl of one to three carbon atoms, inclusive, and phenyl;

X is zero or 1;

$R_1$ and $R_3$ are the same or different and are selected from the group consisting of hydrogen, phenyl and aliphatic of one to about twenty carbon atoms, inclusive, and $R_2$ and $R_4$, are joined together to form an alkylene or alkenylene chain of two to about six carbon atoms, inclusive, unsubstituted or substituted with one to six alkyl groups each of said groups having from one to about four carbon atoms, inclusive.

13. The branched polymer of claim 12 which is an aromatic polycarbonate.

14. The branched polymer of claim 13 which is a bisphenol-A polycarbonate.

15. The branched polymer of claim 12 which is a copolyestercarbonate.

16. The branched polymer of claim 15 wherein the ester group is derived from an aromatic diacid.

17. The branched polymer of claim 15 wherein the ester group is derived from an aliphatic diacid.

18. The branched polymer of claim 13 wherein the branching compound is present in an amount of 0.01 to about 3.0 mole percent, based upon the total amount of dihydric phenol in the polymer.

19. The branched polymer of claim 14 wherein the branching component is 4-Cyclohexene-1,2-dicarboxylic acid, 2-[[[(6-carboxy-3-cyclohexen-1-yl)carbonyl]oxy]methyl]-2-ethyl-1,3-propanediyl ester.

20. A thermoplastic randomly branched aromatic carbonate polymer having incorporated therein a branching component in an amount sufficient to produce a thermoplastic randomly branched polycarbonate which is substantially free of crosslinking wherein the branching component comprises a compound of the formula

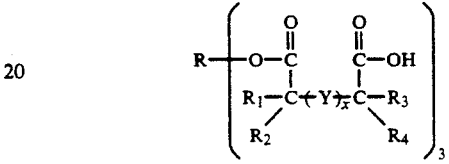

wherein

R is a hydrocarbon of from three to about 50 carbon atoms which component is a product of the reaction of a triol of the formula $R(OH)_3$ with an anhydride of the formula:

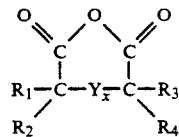

Y is $CR_5R_6$, O, S or $NCH_3$ wherein $R_5$ and $R_6$ are the same or different and are selected from the group consisting of hydrogen, alkyl of one to three carbon atoms, inclusive, and phenyl;

x is zero or 1;

$R_1$, $R_2$, $R_3$, and $R_4$ are the same or different and are selected from the group consisting of hydrogen, phenyl and aliphatic of one to about twenty carbon atoms, inclusive.

* * * * *